US006150128A

United States Patent [19]

Uretsky

[11] Patent Number: 6,150,128

[45] **Date of Patent: *Nov. 21, 2000**

[54] REAGENTS WITH ENHANCED PERFORMANCE IN CLINICAL DIAGNOSTIC SYSTEMS

[75] Inventor: Laura S. Uretsky, Milford, Mass.

[73] Assignee: Bayer Corporation, E. Walpole, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/853,511

[22] Filed: May 9, 1997

Related U.S. Application Data

[63] Continuation of application No. 08/327,856, Oct. 24, 1994, Pat. No. 5,667,983.

[51] Int. Cl.7 .......... C12Q 1/18

[52] U.S. Cl. .......... 435/32; 435/29; 514/372; 540/546; 548/336.5

[58] Field of Search .......... 435/32, 29, 14, 435/4, 25, 15, 817; 514/372, 359, 353, 351, 373, 252, 235.8, 727; 540/546; 548/336.1, 336.5, 146, 161, 327.1

[56] References Cited

U.S. PATENT DOCUMENTS

| | | | |
|---|---|---|---|
| 4,017,631 | 4/1977 | Janssen et al. | 514/727 |
| 4,129,478 | 12/1978 | Racine et al. | 435/817 |
| 4,246,343 | 1/1981 | Wilkins et al. | 435/817 |
| 4,555,400 | 11/1985 | Borovian | 424/78 |
| 4,619,931 | 10/1986 | Heeres et al. | 514/252 |
| 4,650,808 | 3/1987 | May et al. | 514/372 |
| 4,661,503 | 4/1987 | Martin et al. | 524/372 |
| 4,725,587 | 2/1988 | Whitekettle et al. | 514/75 |
| 4,725,623 | 2/1988 | Whitekettle et al. | 514/634 |
| 4,725,624 | 2/1988 | Whitekettle et al. | 514/643 |
| 4,732,905 | 3/1988 | Donofrio et al. | 514/372 |
| 4,732,911 | 3/1988 | Whitekettle et al. | 514/493 |
| 4,732,913 | 3/1988 | Donofrio et al. | 514/528 |
| 4,740,601 | 4/1988 | Ogawa et al. | 548/336 |
| 4,791,111 | 12/1988 | Heeres et al. | 514/252 |
| 4,814,332 | 3/1989 | Klotzer et al. | 548/327.1 |
| 4,845,028 | 7/1989 | Imamura et al. | 435/26 |
| 4,906,651 | 3/1990 | Hsu | 514/372 |
| 4,914,118 | 4/1990 | Donofrio et al. | 514/372 |
| 4,927,833 | 5/1990 | Kirby et al. | 514/399 |
| 5,063,217 | 11/1991 | Whitekettle et al. | 514/75 |
| 5,112,871 | 5/1992 | Austin | 514/727 |
| 5,174,872 | 12/1992 | Scott | 436/74 |
| 5,290,810 | 3/1994 | Austin | 514/727 |
| 5,300,424 | 4/1994 | Hoss et al. | 435/7.1 |
| 5,364,874 | 11/1994 | Morpeta | 514/359 |

FOREIGN PATENT DOCUMENTS

| | | |
|---|---|---|
| 237325 | 7/1986 | Germany . |
| 262978 | 12/1988 | Germany . |
| 3103194 | 4/1991 | Japan . |
| 2018989 | 10/1979 | United Kingdom . |

OTHER PUBLICATIONS

I. Hanning et al., *Improved Blood Compatibility* . . . , Analytical Letters 19 (3&4), pp. 461–478 (1986).

K.S. Chua & I.K. Tan, *Plasma Glucose Measurement* . . . , Clinical Chemistry 24/1, pp. 150–152 (1978).

L.L. Bajema et al., *Detergent–Containing Glucose Oxidase Reagent* . . . , Clinical Chemistry 25/1, pp. 127–129 (1979).

Wallin, Ronnie et al., *Stabilization of Glucose Oxidase* . . . , Chemical Abstracts 122/17, p. 440 (1995).

Denyer et al., International J. of Pharmaceutics, 25(1985) 245–253.

(List continued on next page.)

*Primary Examiner*—Louise N. Leary

[57] ABSTRACT

It has been found that imidazole and related buffers enhance the activity of certain preservatives, for example either (1) a mixture of 5-chloro-2-methyl-4-isothiazolin-3-one and 2-methyl-4-isothiazolin-3-one or (2) 5-bromo-5-nitro-1,3-dioxane, that are used in clinical diagnostic reagents. It has also been found that these buffers and certain surfactants, such as Brij 700 and related hydrophilic surfactants, enhance the precision and accuracy of enzyme biosensors.

17 Claims, 5 Drawing Sheets

3.4 3.2 3.0 2.8 2.6 2.4 2.2 2.0 1.8 1.6 1.4 1.2 1.0 0.8 0.6 0.4 0.2 0 −0.2

0 100 200

□ BUFFER

+ NO BUFFER

OTHER PUBLICATIONS

Kowalski et al, Arch Ophthalmol–vol. 103, Feb. 1985, p250–6.

Uno et al., Antimicrobial Agents & Chemotherapy–vol. 24 No. 4, (1983) p. 552–559.

Wyler et al., InVitro–vol. 15 No. 10, (1979) p. 745–750.

Wilson et al., Biosensors & Bioelectronics 7, (1985) 165–185.

Dempsey, B. and Perrin D.D., Buffers for pH and Metal Ion Control, pp. 1–3,24–25,54–61 (Canberra, Aug., 1973).

Grimmett, M.R., Advances in Imidazole Chemistry, pp. 103–183 (1995), v62.

Neugebauer, Judith, A Guide to the Properties and Uses of Detergents in Biology and Biochemistry, p.1 (1988).

Chapman, John S., American Clinical Laboratory—vol. 13 No. 8, p. 1–2 (1996).

Voo et al, US Patent Application Serial No. 08/245,303 (1994).

Uno et al, "Antimicrobial Agents and Chemotherapy", vol. 24, No. 4, p 552–559, (10–83) (1996).

REAGENTS WITH ENHANCED PERFORMANCE IN CLINICAL DIAGNOSTIC SYSTEMS

This application is a continuation of U.S. application Ser. No. 08/327,856, filed on Oct. 24, 1994 now U.S. Pat. No. 5,667,983.

SUMMARY

It has been found that imidazole and related buffers enhance the activity of certain preservatives, for example either (1) a mixture of 5-chloro-2-methyl-4-isothiazolin-3-one and 2-methyl-4-isothiazolin-3-one or (2) 5-bromo-5-nitro-1,3-dioxane, that are used in clinical diagnostic reagents. It has also been found that these buffers and certain surfactants, such as BRIJ 700 and related hydrophilic surfactants, enhance the precision and accuracy of enzyme biosensors.

BACKGROUND

Clinical diagnostic instruments are those used to measure the presence and quantity of analytes in human blood, serum and other fluids. Examples of analytes that are measured include, but are not limited to, sodium, potassium, calcium, chloride, other electrolytes, glucose, lactate, cholesterol, lipids (e.g., triglycerides), and uric acid. In addition, the instruments are used to measure pH and concentrations of dissolved gases in these fluids. Many other analytes and attributes are also measured by these instruments. Theories identifying new physical and chemical characteristics which are indicators of the state of human health are frequently discovered, and analytical techniques for these new attributes are developed for use on these instruments. The actual component of the instrument which determines the concentration of the analyte of interest is often referred to as the electrode or sensor. Typically the analyte measurement system for these sensors is electrochemical, but could also be optical or could involve measurement of another physical or chemical property. The sensor may at times be complex and combine several systems. For example, an enzyme might be linked to the sensor matrix and catalyze the decomposition of an analyte, generating a component which can then be measured.

The successful measurement of an analyte depends on the interaction of instrument, sensor and reagents. The reagents are particularly important because they can impact the performance of both the sensor and instrument. Some of the reagents necessary for running the analyses on the clinical diagnostic instruments include the calibrators (reagents which have been formulated to contain a specified concentration of the analyte of interest, so that the assay can be run with said calibrator to fix a given response point for the instrument for this concentration), control products (products which are run along with analytical samples to determine if the assay is working properly), and analytical reagents (which include buffers, chemical reactants, etc.) which cause the chemical or physical reaction to occur with the analyte. Other reagents include wash solutions to clean test samples from the instrument. Some of these reagents are formulated in environments that include or simulate the environment of the component being measured. (E.g., some may be formulated in serum at a particular ionic strength and a particular pH. Others may have a particular lipophilic content.) These reagents are the same types of reagents used for manual assays, and, therefore, even though the discussion herein concentrates on reagents for clinical diagnostic instruments, including those that are automated, the same also applies to manual analytical techniques.

Many of the above reagents are formulated with preservatives, in order to extend their shelf life, since the reagents contain nutrients that will support microbial growth. This application deals with the efficacy of a mixed preservative system which has been unexpectedly found to be enhanced in performance when a particular buffer, imidazole or a derivative thereof, is used in the formulation. It also deals with how these buffers and a particular surfactant, BRIJ 700, enhance the precision and accuracy of enzyme biosensors.

DETAILED DESCRIPTION

Figure 1:
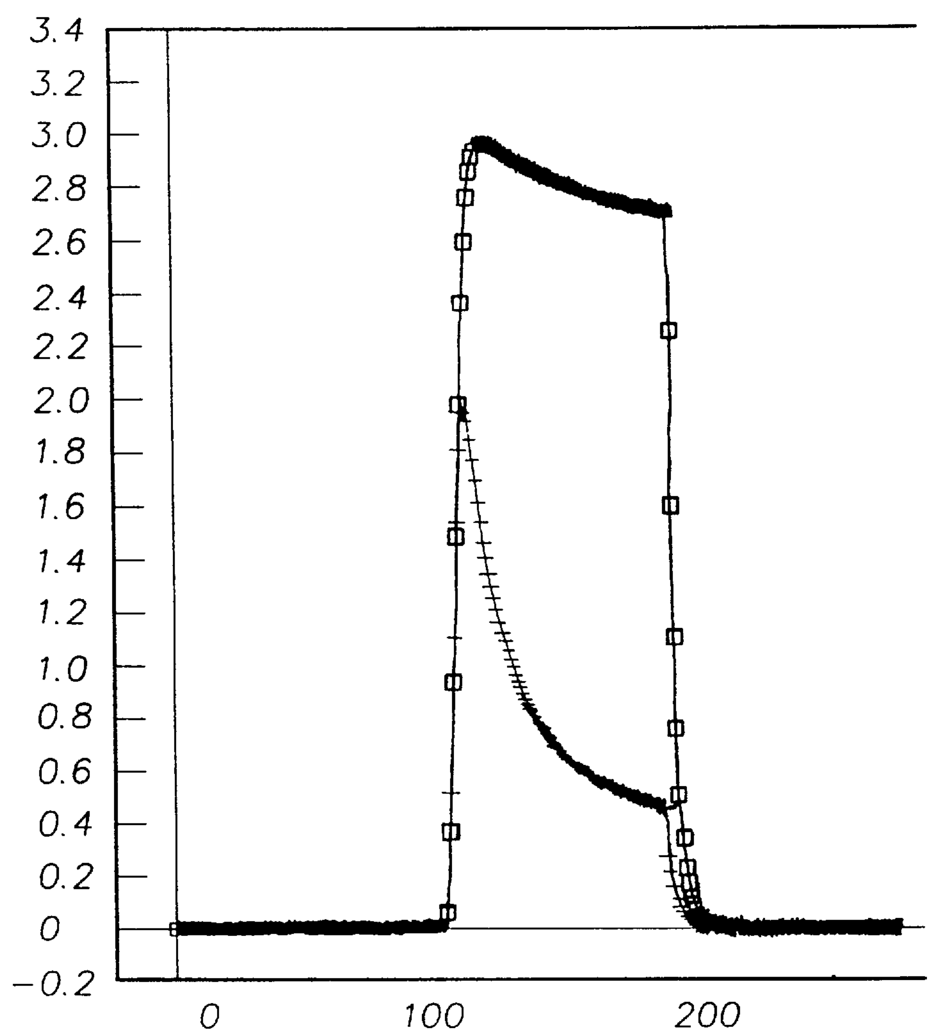
FIG. 1 shows buffered vs. unbuffered response for a glucose biosensor without a glucose diffusion-limiting membrane.

Reagents used for clinical diagnostic purposes contain a variety of components, namely salts (for example, sodium chloride, potassium chloride, calcium acetate, sodium acetate and others in quantities sufficient to provide the desired level of a particular ion), various metabolites (for example glucose and lactate), surfactant, buffer, and water. Not every reagent contains all of these components, and other reagents contain additional ingredients. In particular those that are distributed in commerce frequently contain one or more preservatives in order to extend their shelf life.

Note that any metabolite is a candidate for inclusion in the instant products. However, there are some reactivity and interaction concerns that require some special precautions to be taken. For example, some proteins such as albumin are not always stable in solution, and storage of the potentially unstable solution in the refrigerator may be necessary. In addition, some proteins may bind preservatives and, therefore, reduce the effectiveness of the latter.

Depending on the product, various concentrations of analytes were prepared. The concentration targets were generally either the normal level of the analyte found in the body or abnormal levels (which included low and elevated levels). Several control products might be prepared (e.g., normal and abnormal) which could be used to determine if the sensor worked at both concentration levels. For example, for chloride, where the expected normal range is 70–120 mmol/L, the sensor in a typical instrument can measure over the range of 30 to 150 mmol/L. A "normal" control might be formulated at 100 mmol/L, while the "elevated" control might be formulated at 140 mmol/L. Furthermore, there is an infinite number of combinations of analytes that can be formulated into a control product, depending on the needs of the laboratory. Of course, caution must be exercised to be certain that analytes that might interfere with the analysis of the analyte of interest are excluded or at least are present in such low levels that there are minimal interference effects.

For example, in preparing a chloride control, nitrates and nitrites must be excluded or minimized. In addition, factors that interfere with stability and ease of manufacture should be avoided.

When used in a diagnostic reagent, there are several important aspects of surfactants that must be considered. First, there is a benefit derived from including the surfactant, namely that it improves the washing of portions of the instrument, such as the instrument path and the sensors, which have been exposed to samples, thus reducing the contamination between samples. Second, in selecting the surfactant, it is important to determine that it is compatible with the sensors. Third, surfactants are also commonly used to optimize instrument and sensor performance (e.g., fluidic control, and wet-up or wetting of sensor surfaces). An important aspect of the surfactant that must be evaluated to assure compatibility with a diagnostic system includes determining hydrophilicity/hydrophobicity of the surfactant. Among the surfactants considered was polyoxyethylene (100) stearyl ether. (This is available as BRIJ 700 from ICI Americas and other sources.) The surfactant affects both the sensor and instrument by its hydrophilic/lipophilic character. Lipophilic characteristics are often desired for surfactants in diagnostic systems because washout of lipophilic biological samples and wet-up (hydration) of biosensors requiring water transport are improved. On the other hand, in some systems, such as blood gas and ion sensitive electrodes (ISE), a proper hydrophilic/lipophilic balance is required to prevent wetting and extraction of critical sensor components. Surfactants can be characterized by their hydrophilic/lipophilic character or balance (HLB), which is a measure of relative amount of hydrophilic character. HLB values for nonionic surfactants range from 0–20, where 0 represents 0% hydrophilic character. Surfactants commonly used in diagnostic reagents have HLB values that range from 13–17, and examples of such commonly used surfactants include TRITON X-100 (octylphenoxy polyethoxy ethanol, available from Union Carbide Chemicals and Plastics Co., Inc.), which has an HLB of 13.5; Brij35 (polyoxyethylene(23) lauryl ether, available from ICI Americas), with an HLB of 16.9; and TWEEN 20 (polyoxyethylene(20) sorbitan monolaurate, available from ICI Americas), with an HLB of 16.7.

Hydrophilic surfactants (e.g., BRIJ700), when added to wash and calibrator solutions, were found to provide enhanced precision and accuracy of biosensors during biological sample measurement. Reagents containing more lipophilic surfactants, such as TRITON X-100 and BRIJ35 depressed sensor response to the desired analyte (i.e., slopes were reduced) and caused sensors to exhibit drift when exposed to repetitive biological samples. It is believed that the sensor enhancement effect of BRIJ700 is related to the surfactant hydrophilic/lipophilic balance and partitioning between the sensor and liquid phase. Although somewhat dependent on electrode construction, lipophilic surfactants would have a greater tendency to partition from the aqueous calibrators to the sensor and then desorb into more lipophilic samples (e.g., blood) than hydrophilic surfactants. It is also believed that the surfactant, BRIJ 700, may facilitate the transport of buffer species to the sensor electrode. This can aid in maintaining a constant pH at the enzyme electrode.

It should be noted that the current state of the art is that the use of surfactants causes instability with the performance of specific biosensors, such as glucose and lactate. (See Yellow Springs Instrument, Glucose Lactate Analyzer Users Manual, Model 2300 Stat Plus, February 1992, p. C-3.) As demonstrated in the instant invention, we have discovered a way of utilizing surfactants in order to take advantage of their beneficial properties, without encountering the negatives cited in the Yellow Springs Instrument reference.

In addition to the benefits shown for Brij 700 and related surfactant on the above biosensors, there are similar benefits on many other sensors used in clinical analyzers. In many cases, particularly with calcium and possibly potassium, sensor failure is due to the extraction of one or more components by lipophilic surfactants and protein-containing biological samples. It is believed that Brij 700 and other related hydrophilic surfactants will extend the use life of these sensors due to a reduction in the extraction rate of key critical components.

Many different preservatives have been used in diagnostic reagents. These include, but are not limited to, (a) 5-chloro-2-methyl-4-isothiazolin-3-one, (b) 2-methyl-4-isothiazolin-3-one, and (c) 5-bromo-5-nitro-1,3-dioxane. Mixtures of (a) and (b), in the ratio of approximately 3:1, are commercially available from Rohm & Haas under various tradenames, such as KATHON CG, PROCLIN 300 and PROCLIN 150, which vary from one another by the stabilizer used in formulating the preservative mixture and other factors not affecting the active ingredients. This family of products, to be referred to herein as "Kathon", is a member of the class of preservatives known as isothiazolines, and its performance is representative of this entire class. Preservative (c) is available commercially from Henkel under the tradename BRONIDOX L (if in liquid form) and BRONIDOX K (crystalline form) and will be referred to herein as "Bronidox". Bronidox is a member of, and performs in a way representative of, the class known as nitrobromo compounds.

Many products used in clinical assays must control pH, either to assure that the chemical reaction that takes place is the expected one, or to simulate the pH of the biological fluid being assayed or to assure a stable biosensor response. Controls and calibrators, in particular, are formulated to match, as closely as possible, the serum or other body fluid which is being analyzed. As a result, buffers are used in many clinical diagnostic reagents. Once the desired pH of the reagent is known, the chemist has a number of buffers to choose from. Typically, in the pH range of 6.5 to 7.5, the buffers will be one of the following: phosphate; ACES; ADA; (2-Aminoethyl)trimethylammonium chloride; Arsenic acid; BES; N,N'-Bis(3-sulphopropyl) ethylenediamine; BIS-TRIS; Bis-tris-propane; 2,3-Dihydroxypropyl-tris-(hydroxymethyl)methylamine; Dimethylaminoethylamine; 3,6-Endomethylene-1,2,3,6-tetrahydrophthalic acid; Ethylenediamine; Glycerol-2-phosphoric acid; HEPES; MOPS; MOPSO; p-Nitrophenyl; PIPES; TES; TRIS; and 2,4,6-Trimethylpyridine. (See Perrin et al, Buffers for pH and Metal Ion Control, 1974, Chapman & Hall, Ltd., p. 161, for chemical names of the buffers.) However, certain buffers, although they may control pH in the 6.5 to 7.5 range, are not considered suitable for use in biological systems. For example, imidazole, which has a $pK_a$ of 6.75 at 37° C., is considered too reactive and unstable to be satisfactory in biological systems. (See Perrin et al, ibid. p. 59.)

It has unexpectedly been found that imidazole, a buffer which had hitherto been suspected of being incompatible with biological systems, enhances the antimicrobial activity of a number of preservatives, including Kathon, Bronidox, and mixtures thereof. Imidazole does not itself have any known antimicrobial properties (and testing conducted as part of this work confirmed that no preservative activity was found), yet its use as a buffer in the aforementioned systems improves the antimicrobial capability of the preservatives.

Preferred diagnostic products showing the improvement in antimicrobial activity had pH's ranging from about 6.5 to 7.5 (p$K_a$ of about 6.00 to 8.00) and had buffer capacity of 5 to 50 mmol/L; ionic strength ranged from 0.150 to 0.230; electrolyte values were within normal human ranges (100–150 mmol/L for Na+, 2.0–8.0 mmol/L for K+, 70–120 mmol/L for Cl–, and 0.5–2.00 mmol/L for Ca+). Not only was imidazole found to enhance preservative activity, but also related buffers (e.g., 4-methyl imidazole, which has a p$K_a$ of 7.24 at 37° C.) were found to have a similar effect.

To evaluate the preservative capacity of the products, a series of tests was conducted. First, it should be noted that, even though the goal of the testing was identified as evaluating the preservative capacity, similar testing might be called antimicrobial preservative effectiveness testing. (See U.S. Pharmacopeia for details for minimum inhibitory concentration (MIC), minimum bacteriocidal concentration (MBC) or preservative challenge (PC) testing.) Each preservative has a unique fingerprint of performance activity when one considers a broad cross-range of microorganisms. The testing conducted herein was finite, and only several microorganisms were utilized, but performance on these microorganisms is considered to be representative of their performance on a wide range of microbes. The microbes tested herein were Staphylococcus, Pseudomonas, molds, yeasts and gram positive rods, since these are among the genera most likely to be encountered in the synthesis, use and storage of the products being considered (e.g., control products). The actual microorganisms used in the testing are discussed in more detail in the examples below.

One type of testing conducted to evaluate the antimicrobial efficacy included testing to measure end of life of the preservative. This testing is conducted by allowing the preservatives to degrade to various concentrations and evaluating the efficacy at various levels of concentrations until no activity is found. Thus, the lower the effective concentration of the preservative, the better performing is the preservative system.

The class of preservatives known as Azoles, which are somewhat chemically related to imidazole, do possess antimicrobial activity in the type of products investigated. However, a number of Azoles (e.g., 4-(2-benzimidazolyl) thiazole) were eliminated from consideration as preservatives when evaluated in some products due to appearance and solubility issues. On the other hand, imidazole and related buffers are not known to possess antimicrobial activity.

Broad ranges of Bronidox and Kathon have had their effectiveness enhanced by various levels of Imidazole. Approximately 5–70 mmol/L of Imidazole have been found to enhance the preservative capability from about 30–250 ppm of Bronidox and/or from about 1–25 ppm of Kathon. (Note that there are several different Kathons, differing primarily in type of stabilizer. Most seem to be usable in the invention, particularly Kathon SF (or KSF), also called ProClin 300.) Preferably about 40–60 mmol/L of Imidazole is used to enhance the performance of about 100–250 ppm of Bronidox and/or about 10–25 ppm of KSF. The most preferred composition of the control product is about 48–58 mmol/L Imidazole used to enhance the performance of about 180–220 ppm of Bronidox and/or about 16–20 ppm of KSF.

The compatibility of preservatives and various buffers were tested on solutions used both in manual and automated procedures and in various instruments, including those that utilize sensors or electrodes. There was no detrimental effect noticed on any sensors or on any other component of the instrument.

Figure 2:
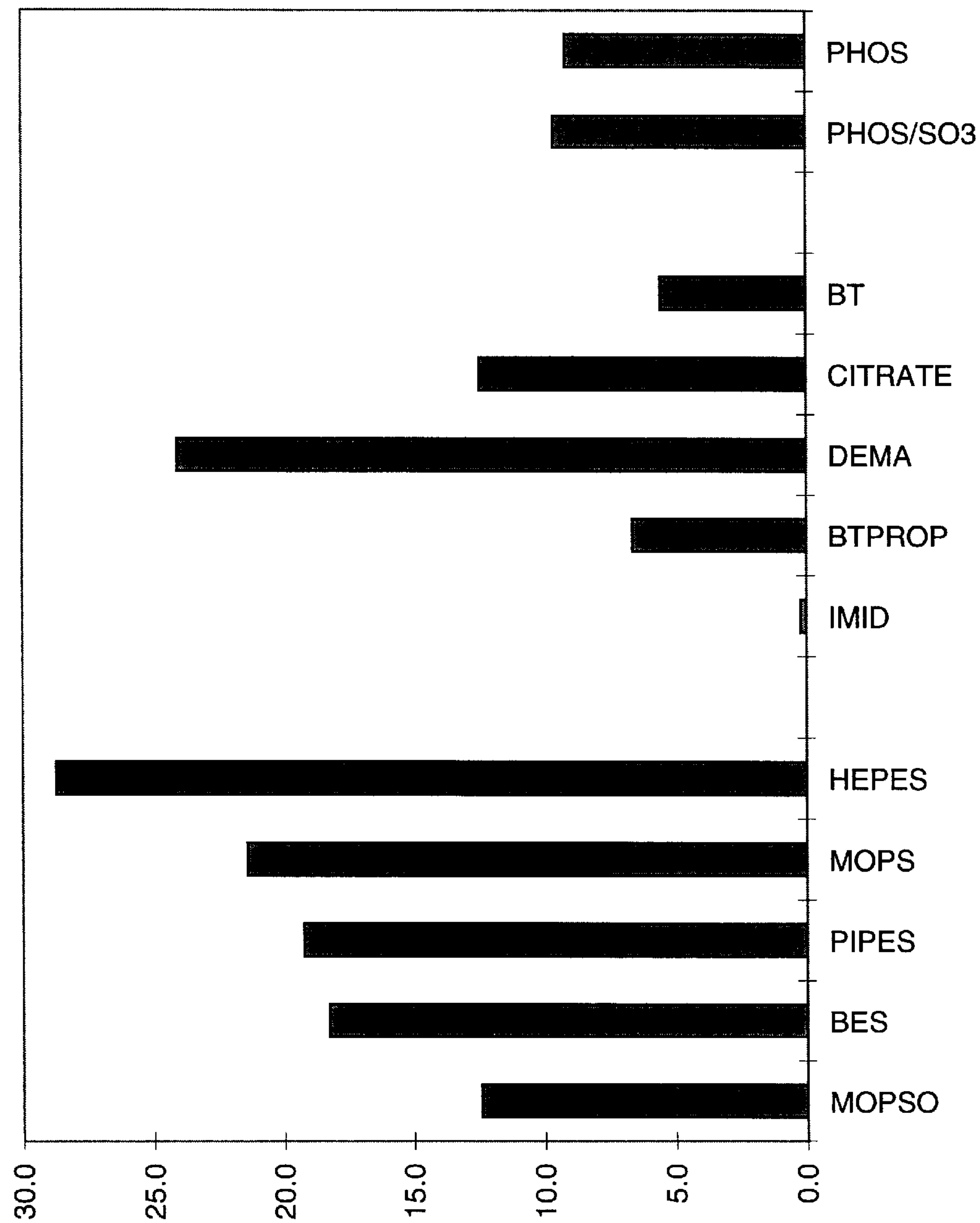
FIG. 2 shows the improved stability in sensor response for imidazole relative to other common buffers used in clinical diagnostic reagents.

An additional and unexpected benefit of imidazole and related buffers is that these buffers stabilize the response of biosensors (e.g., glucose) to aqueous calibrators. Although the mechanism is not understood, it is believed that these buffers control the local sensor pH better than more traditional clinical diagnostic buffers, such as phosphate or zwitterionic buffers. Control of pH is important for biosensor performance, since both enzyme and peroxide oxidation reactions may generate acid, during the enzymatic/analyte reaction and the peroxide detection scheme, and show a dependence on pH. Starting at a pH of 6.8, the peroxide oxidation and the typical biosensor enzyme (glucose oxidase, lactate oxidase) exhibits decreased activity/sensitivity as pH decreases, since acid is generated. In an unbuffered environment, the typical biosensor, such as one for glucose or lactate, will show a drooping response when exposed to the analyte. See FIG. 1, which shows buffered vs. unbuffered response to an aqueous glucose sample for a glucose biosensor without a diffusion-limiting membrane in units of electrical current vs. time in seconds. (The units for electrical current are nanoamps $X10^{-2}$; i.e., the maximum point on the scale is 340 nanoamps.) Experiments performed with a glucose oxidase sensor show that both buffer capacity and type have an effect on the stability of the sensor during measurement. FIG. 2 shows that the response drop is greatly reduced for imidazole relative to other common buffers used in clinical diagnostic reagents. (FIG. 2 shows % drop in glucose reading for several buffers.)

The following examples illustrate various aspects of the enhancing of preservative activity by imidazole and related products and enhancing of biosensor response by the same buffer and Brij 700 and related surfactants. Variations thereof will become apparent to those with skill in the art. These examples are not intended to limit the usefulness of the instant invention.

EXAMPLE 1

Formulation of Control Products

Several analytes were formulated into the following control products:

COMPARISON FORMULATIONS

| CHEMICAL | UNITS | A | B | C | D | E | F |
|---|---|---|---|---|---|---|---|
| IMIDAZOLE | mmol/L | 53 | 5 | 0 | 0 | 0 | 0 |
| 4-METHYL IMIDAZOLE | mmol/L | 0 | 0 | 0 | 0 | 0 | 5 |
| MOPS | mmol/L | 0 | 0 | 0 | 5 | 0 | 0 |
| HEPES | mmol/L | 0 | 0 | 0 | 0 | 5 | 0 |
| NaCl | mmol/L | 67.6 | 91.1 | 96.0 | 96.0 | 96.0 | 91.4 |
| Na Acetate | mmol/L | 72.4 | 48.9 | 44.0 | 42.1 | 41.2 | 48.6 |
| KCl | mmol/L | 4.0 | 4.0 | 4.0 | 4.0 | 4.0 | 4.0 |
| Ca Acetate | mmol/L | 1.25 | 1.25 | 1.25 | 1.25 | 1.25 | 1.25 |
| HCl, conc. | mmol/L | 28.4 | 2.4 | 0.0 | 0.0 | 0.0 | 2.0 |
| NaOH, 10N | mmol/L | 0 | 0 | 0 | 1.9 | 2.8 | 0 |
| Li Acetate | mmol/L | 0.0 | 45.5 | 12.3 | 50.3 | 50.3 | 50.3 |
| GLUCOSE | mmol/L | 10.0 | 10.0 | 0.0 | 10.0 | 10.0 | 10.0 |
| Li LACTATE | mmol/L | 2.0 | 2.0 | 0.0 | 2.0 | 2.0 | 2.0 |
| PROCLIN | ppm | 18 | 18 | 18 | 18 | 18 | 18 |
| Bronidox K | ppm | 200 | 200 | 200 | 200 | 200 | 200 |
| SURFACTANT | % | 0.2 | 0.2 | 0.2 | 0.2 | 0.2 | 0.2 |

The products were prepared by dissolving the reagents in water and stirring until all were completely dissolved. Care should be taken to ensure that there is complete dissolution of all the components, especially surfactants and preservatives. In addition, the pH of the solution should be appropriate to maintain the stability of, and to allow for solubility of, each component as it is added.

EXAMPLE 2

Analysis of Control Products

The control products were tested by using them within the manual assays or on the instruments where they will be used. Values are assigned by testing over several instruments or manual assay runs. Calibrators are assigned values by the reference methods or a recognized alternative for each analyte. For example, the sodium and potassium values are assigned by flame photometry.

| | | ANALYTE VALUES | | | | | |
|---|---|---|---|---|---|---|---|
| PARAMETER | UNITS | A | B | C | D | E | F |
| pH | pH | 6.8 | 6.8 | 7.15 | 6.8 | 7.4 | 7.4 |
| IONIC STRENGTH | mmol/L | 200 | 200 | 200 | 200 | 200 | 200 |
| SODIUM | mmol/L | 140 | 140 | 140 | 140 | 140 | 140 |
| POTASSIUM | mmol/L | 4.0 | 4.0 | 4.0 | 4.0 | 4.0 | 4.0 |
| CALCIUM | mmol/L | 1.25 | 1.25 | 1.25 | 1.25 | 1.25 | 1.25 |
| CHLORIDE | mmol/L | 100 | 100 | 100 | 100 | 100 | 100 |
| GLUCOSE | mmol/L | 10.0 | 10.0 | 10.0 | 10.0 | 10.0 | 10.0 |
| LACTATE | mmol/L | 2.0 | 2.0 | 2.0 | 2.0 | 2.0 | 2.0 |
| BUFFER CONC. | mmol/L | 53.0 | 5.0 | 0.0 | 5.0 | 5.0 | 5.0 |
| proclin 300 | ppm | 18 | 18 | 18 | 18 | 18 | 18 |
| Bronidox K | ppm | 200 | 200 | 200 | 200 | 200 | 200 |

EXAMPLE 3

Shelf Life of the Products

The shelf life of the product is one measure of the efficacy of the preservative system. Shelf life is based in part on end of life MBC/PC testing to establish a minimum concentration needed to provide total kill of selected organisms at 24 hours. These concentrations are then used within an Arrhenius analysis to determine how long the reagent will be viable. For more effective preservative systems, a longer shelf life for the product is expected. In addition, in the end of life testing, the lower the concentration needed to achieve this killing of microorganisms, the more effective is the preservative system. See the table below, which evaluated two different buffer systems. (End of Life testing indicates the minimum amount of preservative necessary to totally kill microorganisms within 24 hours.) Therefore, the lower end of life concentration observed in the presence of an imidazole buffer indicates that imidazole enhances the microbial efficacy of Kathon. (Note that the 33.7 ppm is essentially equivalent to 30.5 for end of life data.)

| | SHELF LIFE YEAR @ 25° C. | | END OF LIFE MBC/PC (ppm) | |
|---|---|---|---|---|
| BUFFER | KATHON | BRONIDOX | KATHON | BRONIDOX |
| MOPS | 0.8 | 1.3 | 6.23 | 30.5 |
| IMIDAZOLE | 2.3 | 3.7 | 1.30 | 33.7 |

EXAMPLE 4

The Use of Glucose Biosensors

Biosensor experiments were performed using glucose sensors in either a lab-bench manual sample injection system or on a clinical analyzer. The glucose sensor used was a three pole device consisting of a platinized carbon anode, Ag/AgCl reference, with a platinum counter electrode. The enzyme glucose oxidase (GOD) was applied to the anode by adsorption to the surface or admixing during anode fabrication. The biosensor was protected from fouling by using a glucose limiting membrane, e.g., silicone, polyurethane, cellulose acetate, Nafion, polyester sulfonic acid (Kodak AQ), hydrogels or any other membrane known to those skilled in the art.

Evaluation of Effect of Surfactants on Response of Biosensors

Reagents containing the surfactants Triton X-100 and Brij35 were evaluated to determine their effect on the response of a typical biosensor (e.g., glucose). The data is shown in the table below, where it is shown that Triton X100 depresses the slope more than the Brij35.

| Calibrant Surfactant | Glucose sensor Slope - nA/mg/dL | % change |
|---|---|---|
| no surfactant | 0.69 | 0% |
| Brij35 | 0.63 | 9% |
| Triton X100 | 0.54 | 22% |

Figure 3:
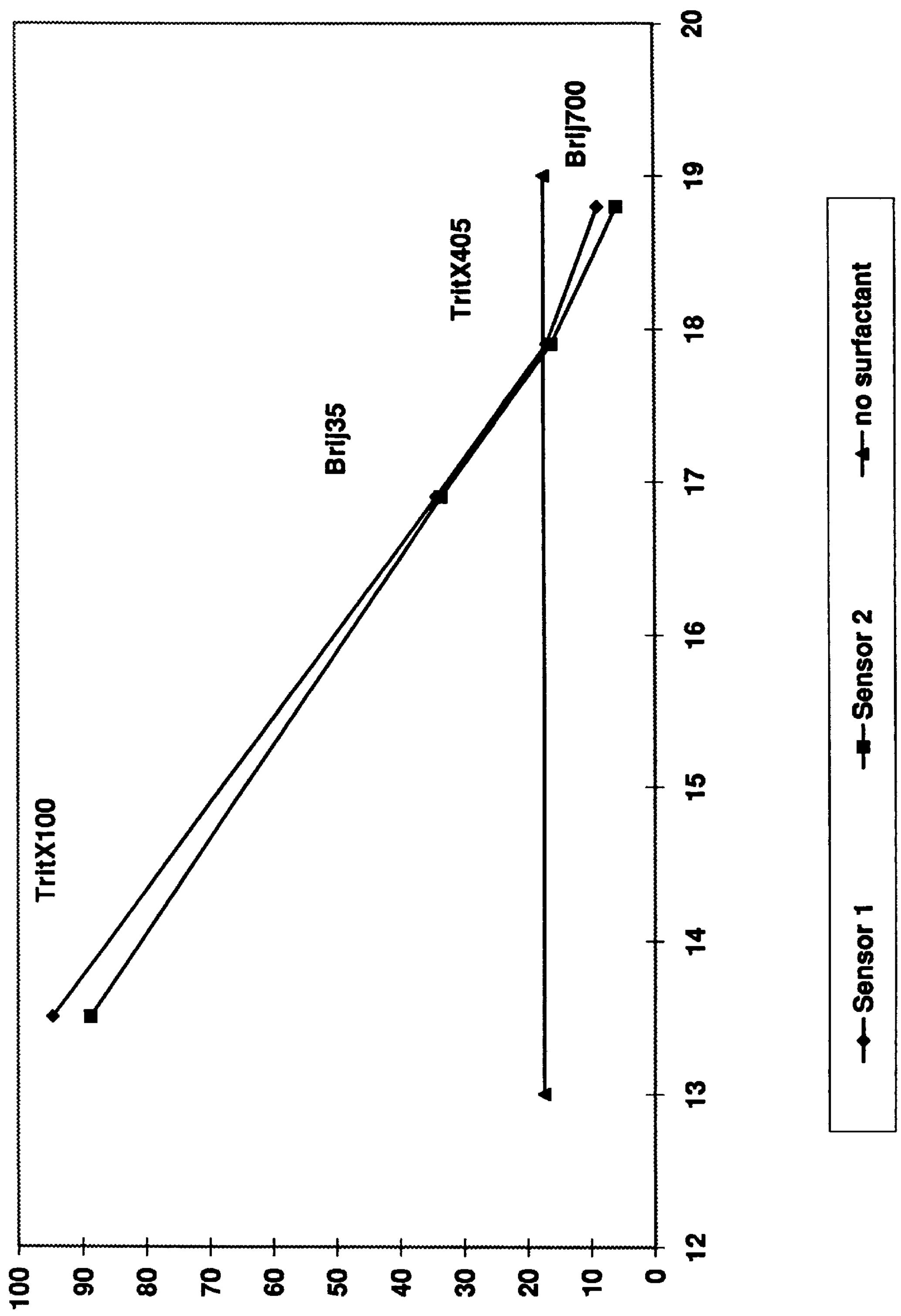
FIG. 3 shows the % change (positive drift) in sensor response over 10 blood samples as a function of surfactant HLB, with results being obtained on a lab-bench test system.
Figure 4:
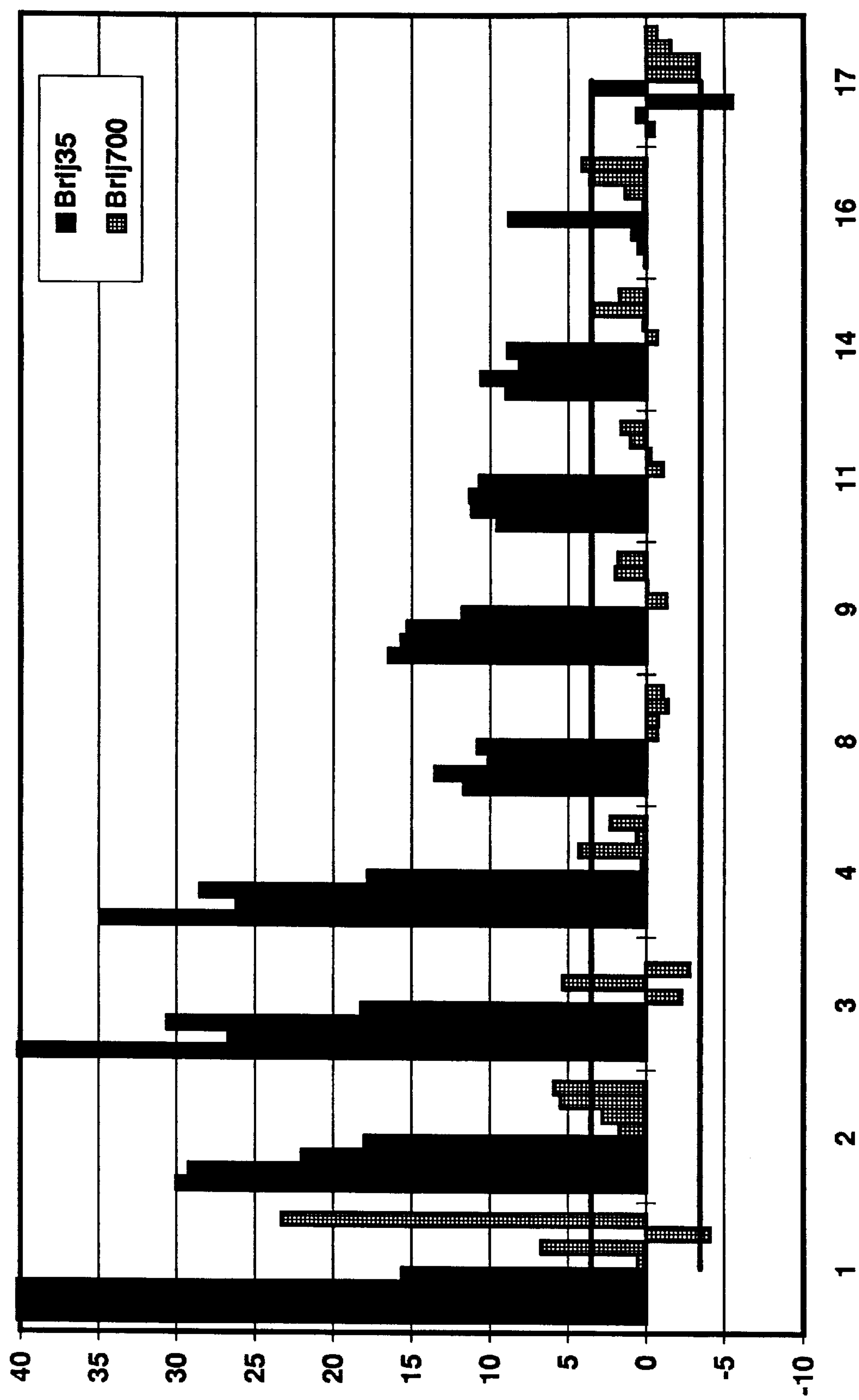
FIG. 4 shows a comparison of the performance of glucose biosensors with BRIJ35 and BRIJ700.
Figure 5:
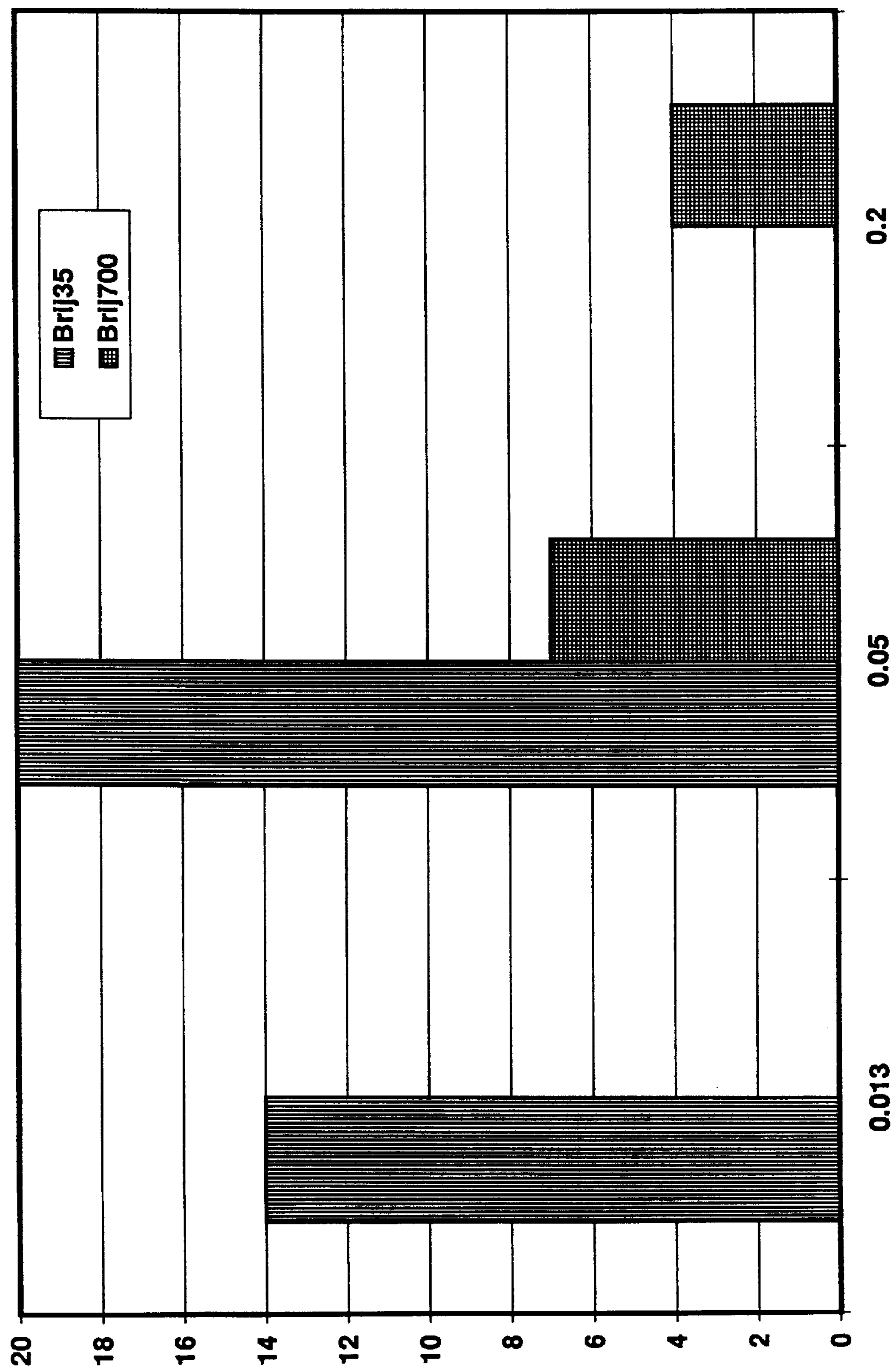
FIG. 5 shows sensor response to equimolar and equal weights of BRIJ 35 and BRIJ700.

After conditioning with one of the surfactants, the sensors exhibited a positive drift in slope when exposed to repetitive biological samples. The magnitude of the drift was found to correlate directly to the HLB of the surfactant. FIG. 3 shows the % change (positive drift) in sensor response over 10 blood samples as a function of surfactant HLB, with results being obtained on a lab-bench test system. The data shows that when sensors are exposed to surfactants having an HLB>18, drifts are comparable to or less than obtained in the absence of any surfactant. Brij700, the preferred surfactant for the invention, minimizes sensor drift over the sensor life. (FIG. 4 shows a comparison of the performance of glucose biosensors with Brij35 and Brij700, using units of % drift vs. time in days. Each time shows the data for four sensors evaluating each of the two surfactant systems.) The concentration of the surfactant is also important, with increased concentration of Brij700 showing reduced drift vs the increased drift observed with increasing Brij35. This is demonstrated in FIG. 5, which shows sensor response to equimolar and equal weights of Brij 35 and Brij700 in terms of% drift. Concentrations evaluated for Brij700 ranged from 0.01–1.0 wt %, while the preferred range was found to be 0.1–0.3 wt %.

The formulations of calibrant and wash solution used to provide enhanced performance of clinical diagnostic sensors (e.g., enzyme biosensors) are shown below.

| Chemical | Units | calibrant | wash | range | preferred |
|---|---|---|---|---|---|
| Imidazole | mmol/L | 53.0 | 0.0 | 10–100 | 40–60 |
| Brij700 | % wt | 0.2 | 0.2 | 0.01–1.0 | 0.1–0.3 |

What is claimed is:

1. A method of enhancing the antimicrobial activity of products comprising isothiazolines or nitrobromo compounds comprising the steps of:

preparing a formulation comprising isothiazoline or a nitrobromo compound; and including in said formulation a buffer system comprising imidazole or monoalkyl derivatives thereof.

2. The method of claim 1 wherein said products comprise both isothiazolines and nitrobromo compounds.

3. A method of claim 2 wherein the products are clinical diagnostic reagents.

4. A method of claim 3 wherein the isothiazoline is a mixture of 5-chloro-2-methyl-4-isothiazolin-3-one and 2-methyl-4-isothiazolin-3-one.

5. A method of claim 4 wherein the concentration of said isothiazolines is approximately between 1 and 25 parts per million of solution.

6. The method of claim 5 wherein said concentration is approximately between 10 and 25 ppm.

7. The method of claim 6 wherein said concentration is approximately between 16 and 20 ppm.

8. A method of claim 3 wherein the nitrobromo compound is 5-bromo-5-nitro-1,3-dioxane.

9. A method of claim 8 wherein the 5-bromo-5-nitro-1,3-dioxane is present at a concentration of approximately between 30 and 250 parts per million of solution.

10. The method of claim 9 wherein said 5-bromo-5-nitro-1,3-dioxane is present approximately between 100 and 250 ppm.

11. The method of claim 10 in which said 5-bromo-5-nitro-1,3-dioxane is present approximately between 180 and 220 ppm.

12. The method of claim 1 in which said buffer system is present from approximately 5 to 70 mmol/L of solution.

13. The method of claim 12 in which said buffer is present from approximately 40 to 60 mmol/L solution.

14. The method of claim 13 in which said buffer is present from approximately 48 to 58 mmol/L.

15. An antimicrobial system for clinical diagnostic reagents comprising (1) isothiazolines or nitrobromo compounds and (2) imidazole or monoalkyl derivatives thereof.

16. A method of enhancing the antimicrobial activity of products comprising isothiazolines or nitrobromo compounds by including in said products a buffer system comprising imidazole or 4-methyl imidazole.

17. An antimicrobial system for clinical diagnostic reagents comprising (1) isothiazolines or nitrobromo compounds and (2) imidazole or 4-methyl imidazole.

* * * * *

UNITED STATES PATENT AND TRADEMARK OFFICE
CERTIFICATE OF CORRECTION

PATENT NO. : 6,150,128
DATED : November 21, 2000
INVENTOR(S) : Laura S. Uretsky

It is certified that error appears in the above-identified patent and that said Letters Patent is hereby corrected as shown below:

Column 6,
Line 59, Example 1, "PROCLIN" should read -- PROCLIN 300 --; and

Column 7,
Line 30, Example 2, "proclin" should read -- Proclin --.

Signed and Sealed this

Twenty-fifth Day of December, 2001

Attest:

JAMES E. ROGAN
*Director of the United States Patent and Trademark Office*

*Attesting Officer*